United States Patent [19]

Hedman et al.

[11] Patent Number: 4,759,769
[45] Date of Patent: Jul. 26, 1988

[54] ARTIFICIAL SPINAL DISC

[75] Inventors: Thomas P. Hedman; John P. Kostuik, both of Toronto; Geoffrey R. Fernie; Brian E. Maki, both of Islington, all of Canada

[73] Assignee: Health & Research Services Inc., Etobicoke, Canada

[21] Appl. No.: 64,621

[22] Filed: Jun. 22, 1987

[30] Foreign Application Priority Data

Feb. 12, 1987 [CA] Canada ................................ 529548

[51] Int. Cl.⁴ .............................................. A61F 2/44
[52] U.S. Cl. .................................................. 623/17
[58] Field of Search ...................... 128/69; 623/17, 49

[56] References Cited

U.S. PATENT DOCUMENTS 3,426,364  2/1969  Lumb ..................................... 623/17
4,349,921  9/1982  Muntz .................................... 623/17
4,401,112  8/1983  Rezaian .................................. 623/17
4,605,417  8/1986  Fleischauer ............................ 623/49

Primary Examiner—Richard J. Apley
Assistant Examiner—James Prizant
Attorney, Agent, or Firm—Rogers, Bereskin & Parr

[57] ABSTRACT

An artificial disc for a human spine. The disc has upper and lower members hinged together at their rear portions and biased apart at their fronts by stiff coil springs. Rear stop surfaces limit the opening movement of the members. Vertically projecting tabs at the front and side of each member are rigidly screwed to the adjacent vertebrae. Tolerances in the hinge allow limited side to side rocking. The disc and screws are made of titanium alloy or cobalt chrome alloy. In a modified version a hinge pin is replaced by cables tying the members together.

18 Claims, 7 Drawing Sheets

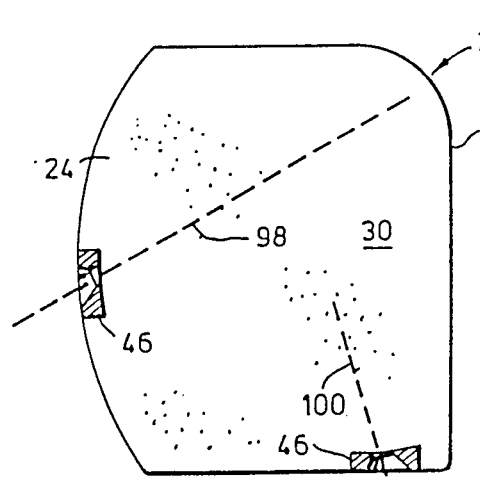
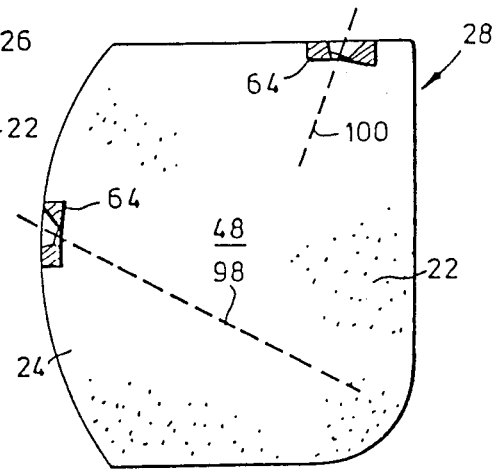
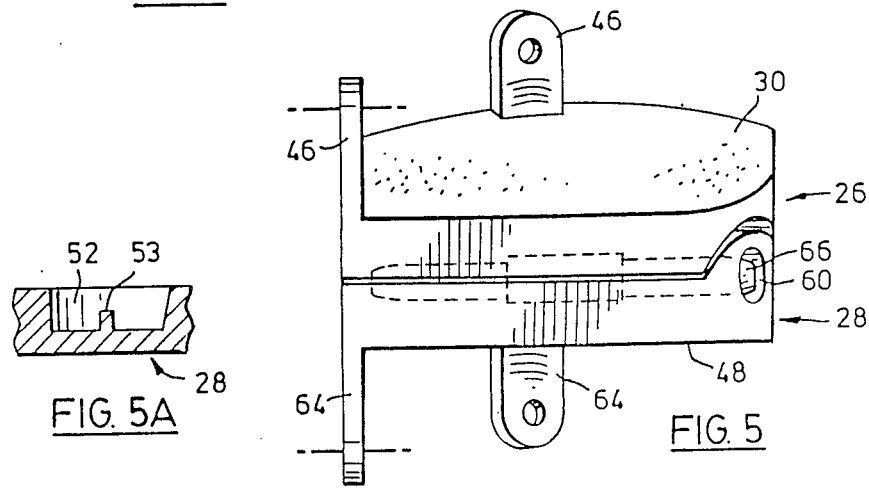
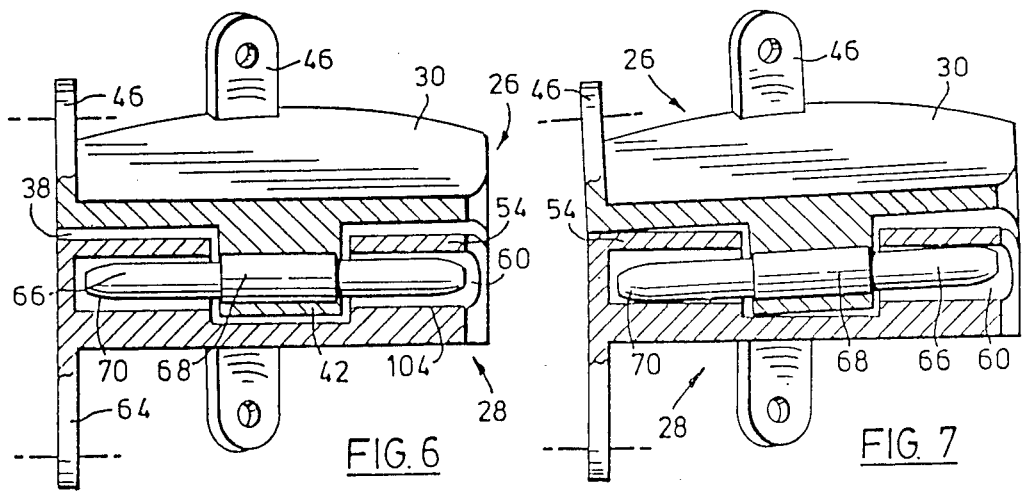

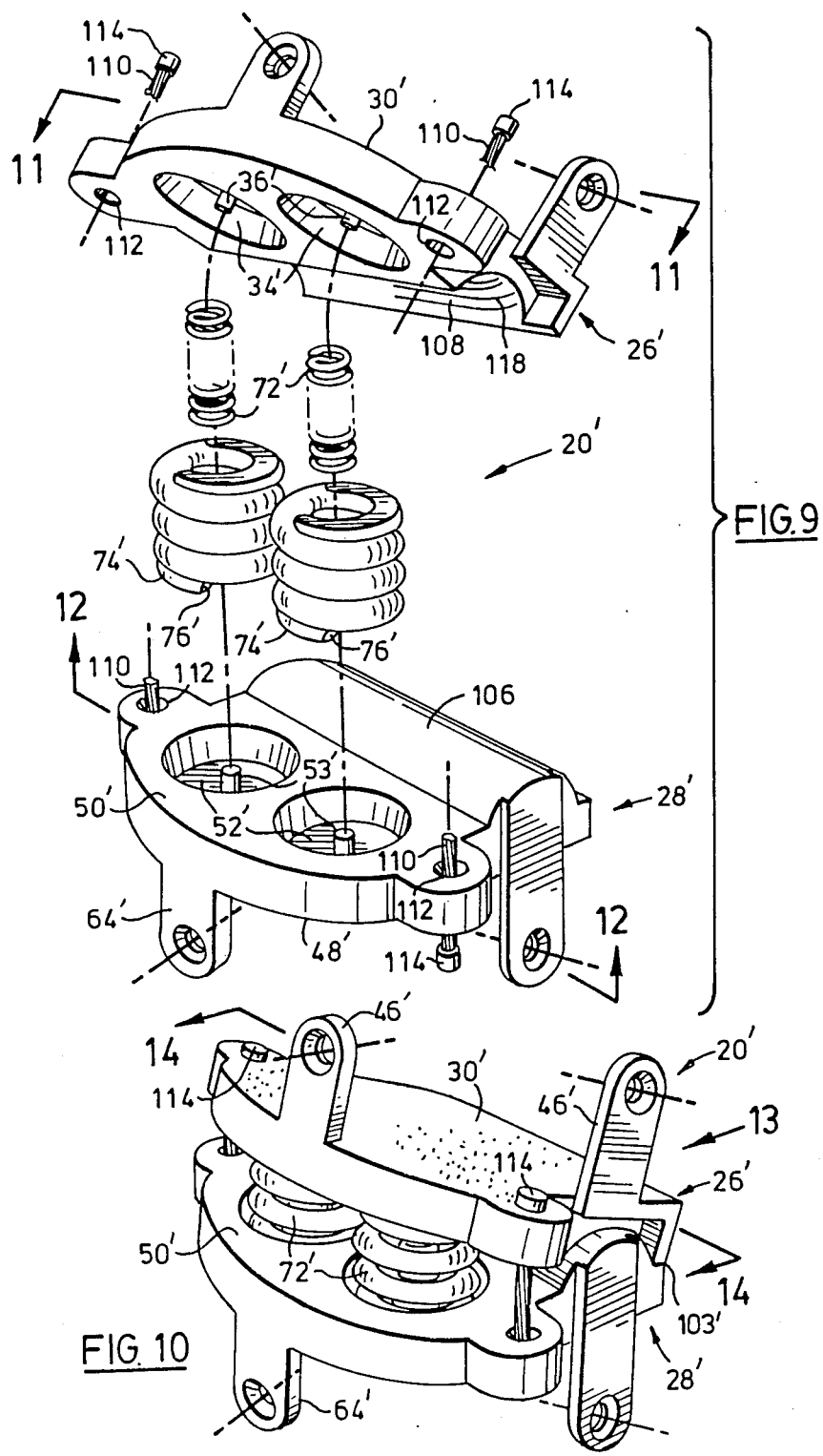

ARTIFICIAL SPINAL DISC

FIELD OF THE INVENTION

This invention relates to an artificial disc for a human spine.

BACKGROUND OF INVENTION

Human spines are formed from vertebrae which are separated and cushioned from each other by discs. The discs consist of a fibrous outer envelope containing a gel-like fluid. The discs are subject to large forces, which may vary from about 175 pounds when a person is at rest to as high as about 500 pounds. For example, a person who lifts a 15 pound weight one foot in front of such person, using a bending movement, can generate nearly 500 pounds of force on his or her spine. Because of the high forces on them, spinal discs commonly rupture, particularly as they deteriorate with age.

Various attempts have been made to deal with the problem of a ruptured disc. One standard procedure is to remove the disc and fuse the vertebrae which were formerly separated by the disc. A difficulty with this is that relative motion between the two vertebrae is no longer possible, causing both stiffness in the spine and difficulties in areas above and below the fused discs.

Other attempts to deal with the problem have involved removing the ruptured disc and replacing it with an artificial resilient pad made e.g. of high density polyethylene or of a silicone material. Such pads tend to wear out rapidly, since a spinal disc typically undergoes goes between one and five million cycles of compression and extension per year. In addition they provide no compliance or natural restoring force, and they do not offer the constraints to movement which are provided by a natural disc.

Another attempted solution has been made to use ball bearings in place of discs. However no satisfactory method has been developed for retaining the ball bearings in place.

SUMMARY OF THE INVENTION

It is therefore an object of the invention to provide an artificial disc which will offer improved performance and a longer lifetime in a patient. In one of its aspects the present invention provides: an artificial disc for a human spine, said disc being adapted to replace a natural disc and to be located between two vertebrae, said disc comprising:

(a) upper and lower members, each having a rear portion and a front portion, (b) said upper and lower members having hinge-like means adapted to permit a hinging motion of said upper and lower members relative to each other about said rear portions, (c) spring means positioned between said upper and lower members and biasing said front portions apart, (d) means securing said upper and lower members together and for permitting said hinging motion, (e) said upper member having means for rigidly securing said upper member to a first vertebrae above said upper member, and said lower member having means for rigidly securing said lower member to a second vertebrae below said lower member.

Further objects and advantages of the invention will appear from the following description, taken together with the accompanying drawings.

BRIEF DESCRIPTION OF DRAWINGS

In the accompanying drawings:

FIG. 3 is a plan view, partly in section, taken along lines 3—3 of FIG. 1;

FIG. 4 is a plan view, partly in section, taken along lines 4—4 of FIG. 1;

FIG. 5 is a rear view taken in the direction of arrow 5 of FIG. 2;

FIG. 5A is a cross-sectional view of a portion of a lower member of the disc of FIG. 1;

FIG. 6 is a rear view, partly in section, taken along lines 6—6 of FIG. 2;

FIG. 7 is a view similar to that of FIG. 6 but showing the upper and lower members of the artificial disc tilted sideways with respect to each other;

FIG. 9 is a perspective exploded view of a second embodiment of an artificial disc according to the invention;

FIG. 10 is a perspective view of the disc of FIG. 9 in assembled condition;

DESCRIPTION OF PREFERRED EMBODIMENTS

Figures 1, 2:
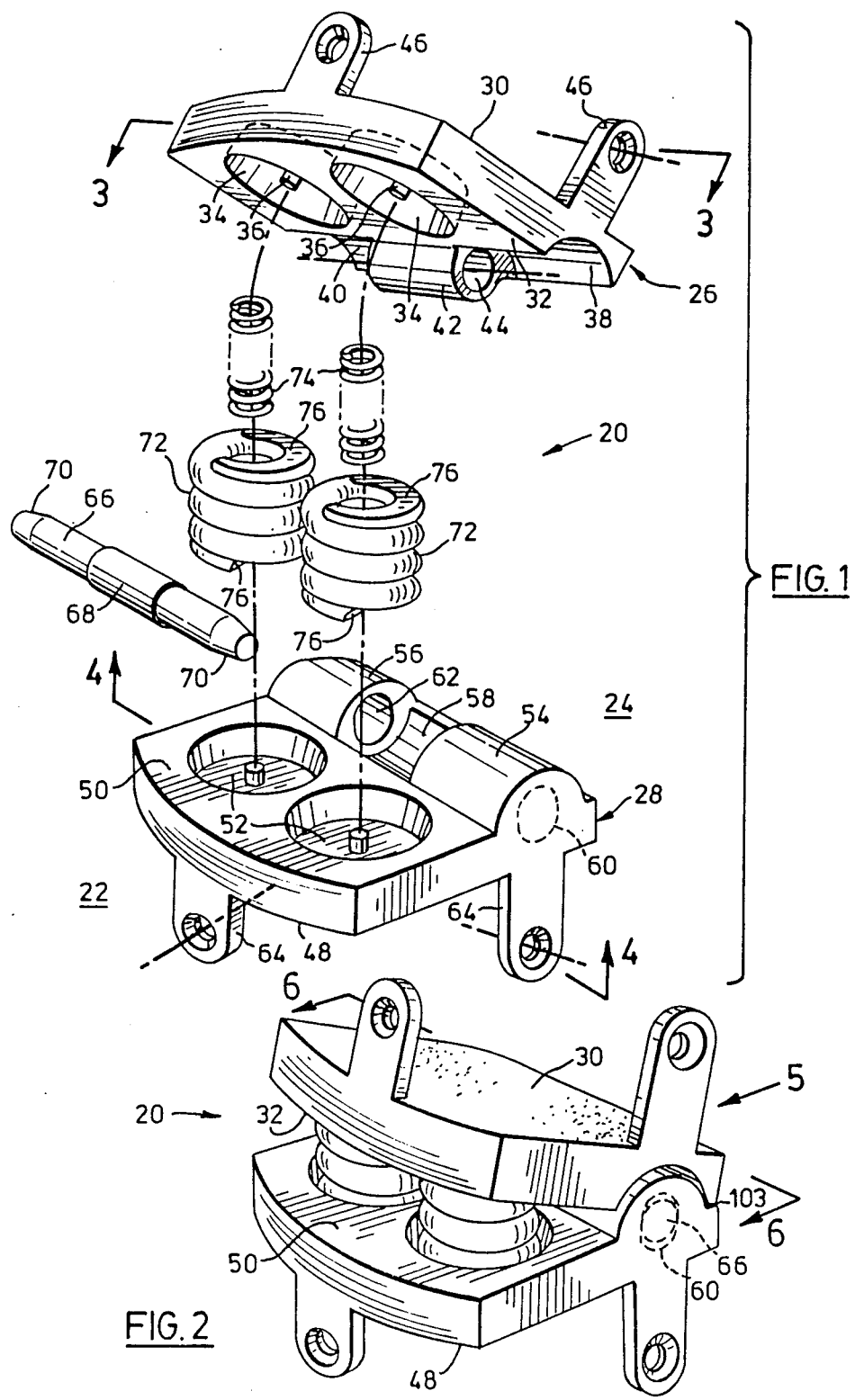
FIG. 1 is a perspective exploded view of an artificial disc according to the invention.
FIG. 2 is a perspective view of the disc of FIG. 1 in assembled condition.

Reference is first made to FIGS. 1 to 7, which show an artificial disc 20 according to the present invention. The front of the disc 20 is indicated at 22 and the rear of the disc at 24.

The disc 20 includes upper and lower members 26, 28 respectively. The upper member 26 includes a substantially flat upper surface 30 and a lower surface 32. The lower surface 32 has at its front portion two cylindrical side-by-side recesses 34, each having a centering post 36 projecting downwardly from the center thereof.

At the rear of the upper member 26, the lower surface 32 further includes at each side thereof a semicy;indrical laterally extending channel 38, 40. The channels 38, 40 are separated by a downwardly projecting semi-cylindrical hinge formation 42 having an axial aperture 44 therein for a hinge pin. Two tabs 46 extend upwardly from the upper surface 30, one at the front and one at the side of the upper member 26.

The lower member 28 includes a substantially flat lower surface 48 and an upper surface 50 which has at its front two cylindrical recesses 52 aligned below the recesses 34. A centering post 53 projects upwardly from the center of each recess 52. At its rear the upper surface 50 of the lower member 28 includes two laterally extending semi-cylindrical hinge formations 54, 56, one at each side thereof, separated by a semi-cylindrical channel 58. Each hinge formation 54, 56 includes an axial recess 60, 62 respectively therein. The recesses 60, 62 have in cross section the form of an elongated circle. Projecting downwardly from the lower surface 48 of the lower member 28 are two tabs 64, one at the front and one at the side thereof.

The artificial disc 20 is assembled by placing the hinge formation 42 in the channel 58 and inserting a hinge pin 66 through the apertures 44, 60, 62. The hinge pin 66 is secured in place by its enlarged central section 68, which is an interference or press fit in aperture 44. The hinge pin 66 is inserted into the left hand side of the disc as drawn in FIGS. 1 and 2; the right hand side of aperture 44 is closed as shown. The ends of the hinge pin are tapered as shown at 70, for a reason to be explained.

The upper and lower members 26, 28 are biased apart about the hinge pin 66 by two pairs of helical compression or coil springs which are located in the recesses 34, 52. Each pair of coil springs consists of an outer coil spring 72 and a concentric inner coil spring 74. The inner coil springs 74 fit over the centering posts 36, 53 to ensure that the springs remain in position. The outer coil springs 72 are held in place primarily by their fit within the recesses 34, 52 and have little or no contact with the inner coil springs 74. The outer springs 72 have bevelled upper and lower ends 76 to provide better and more compact seating.

It is noted that the rear or posterior sides of the recesses 34, 52 slope rearwardly at an angle of between 10 and 20 degrees (FIG. 5A) to accommodate the arc which the springs form as the disc members open and close.

Figure 8:
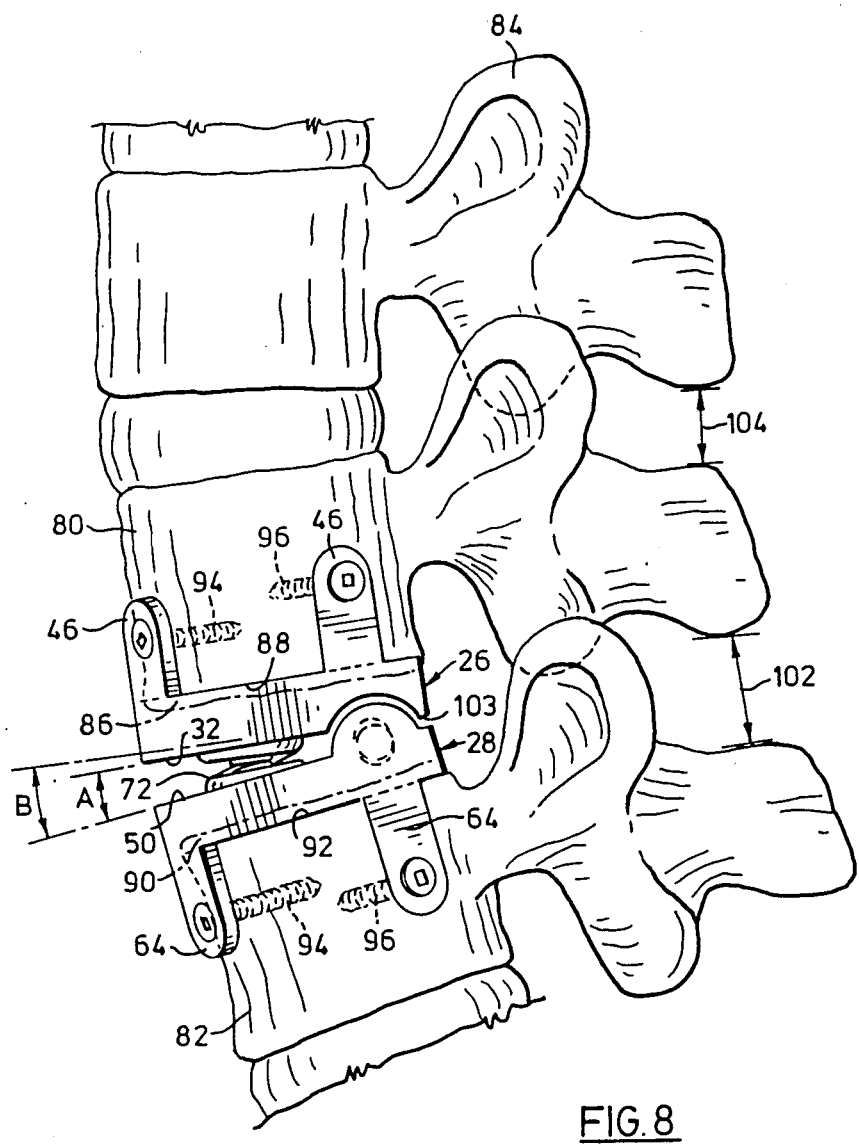
FIG. 8 is a perspective view showing the artificial disc of FIG. 1 assembled in a spine.
Figures 11, 12:
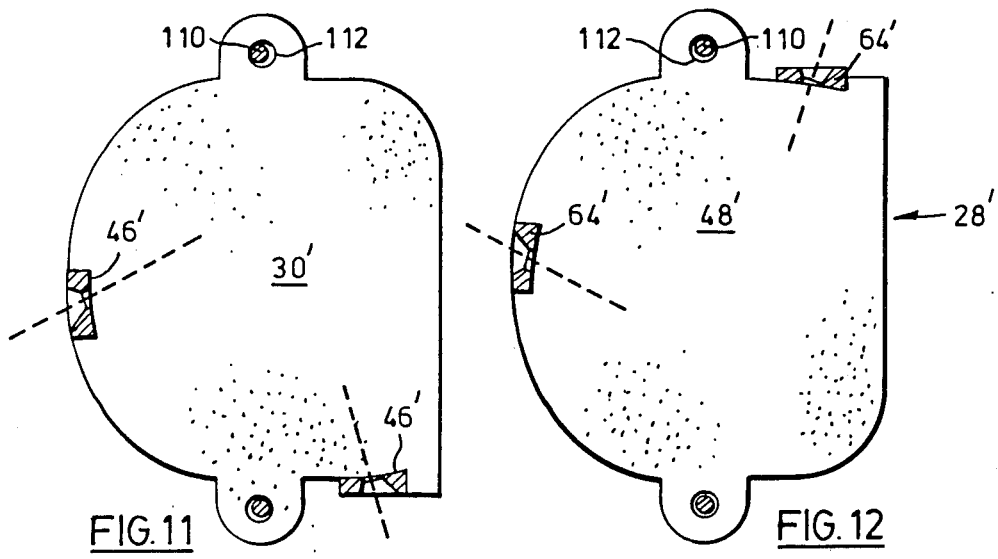
FIG. 11 is a plan view, partly in section, taken along lines 11—11 of FIG. 9.
FIG. 12 is a plan view, partly in section, taken along lines 12—12 of FIG. 9.
Figure 13:
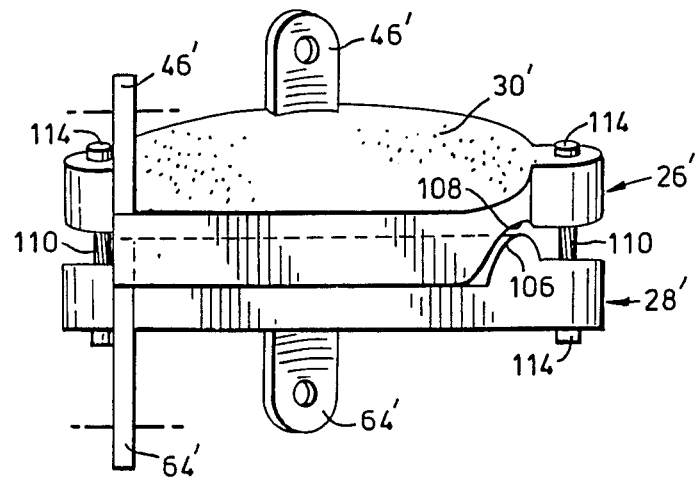
FIG. 13 is a rear view taken in the direction of arrow 13 of FIG. 10.

The artificial disc 20 is installed in a human spine as shown in FIG. 8. As shown, the disc 20 is installed between an upper vertebrae 80 and a lower vertebrae 82. During the installation process, the natural disc is first removed, leaving the natural envelope of ligaments and muscles around the spine as intact as possible. The spinal canal itself runs through the posterior or rear portions 84 of the vertebrae and is not disturbed. Next, the lower portion of the upper vertebrae 80 indicated by dotted lines 86 is removed to provide a flat lower surface 88 of the upper vertebrae for attachment of the upper member 26. The same procedure is followed for the lower vertebrae 82, i.e. its upper portion shown in dotted lines at 90 is removed leaving a flat upper surface 92 for attachment of the lower member 28.

Next, the artificial disc 20 is installed and is secured by front screws 94 and side screws 96 which extend through the tabs 46, 64 and into the respective vertebrae. Since the outer wall portion of each vertebrae is the strongest (the central portion of the vertebrae can be very weak), each screw 94, 96 is made long enough to extend entirely through the vertebrae. Thus, each screw 94, 96 extends through the wall of the vertebrae adjacent the entry point of the screw, through the center of the vertebrae, and through substantially the entire opposite wall of the vertebrae (but does not exit therefrom). The front screws 94 are angled to the side as indicated by lines 98 in FIGS. 3 and 4, so that they extend through as much of the vertebrae as possible and yet will not interfere with the spinal canal should they be slightly longer than necessary. The side screws 96 are angled to the front as indicated by lines 100 in FIGS. 3 and 4, so that they will pass closer to the center of the vertebrae for extra strength. The front and side screws for each member are at different levels (as indicated by the tabs 64 in FIGS. 5 to 7) so that they do not interfere with each other.

In addition the upper surface 30 of the upper member 26 and the lower surface 48 of the lower member 28 are preferably coated with porous material such as sintered metal powder, balls or mesh, as is well known in the art, so that the bone will grow into the porous metal and form a stronger bond with the artificial disc.

It will be noted that the artificial disc 20 occupies slightly more height than a conventional disc. This is indicated in FIG. 8, where the space 102 between the rearmost facets of the vertebrae 80, 82 is indicated as being larger than the space 104 between the rearmost facets of the adjacent pair of vertebrae. This additional height is deliberately built into the artificial disc 20, since the rear or posterior facets 84 of spinal vertebrae tend to be pain centers. The increased height of disc 20 reduces the transmission of loads through the facets, to reduce the likelihood of pain.

In use, with the patient erect, the artificial disc 20 normally assumes the position shown in FIG. 8, with the two members 26, 28 oriented at angle A with respect to each other. Angle A is normally approximately 14 degrees for lumbar vertebrae. When the patient leans backwards, the angle between members 26, 28 is normally that shown at B, which is approximately 20 degrees. Backwards bending is limited by the rear ends of upper and lower surfaces 32, 50, which together form a stop indicated at 103 in FIG. 8 to prevent members 26, 28 from opening too widely with respect to each other. When the patient leans forward, the angle normally closes to approximately 0 degrees.

A natural spinal disc normally provides considerable compliance, typically roughly 1.5 foot pounds per degree of compression. To simulate this compliance, the springs 72, 74 are made very stiff. Typically the spring constant of each outer coil spring 72 is about 1675 pounds per inch and that of each inner coil spring 74 is about 200 pounds per inch (so that the total spring constant is about 3750 pounds per inch). The spring constants can be adjusted, depending on the patient, so that the spring creates a resistive torque (with reference to the angles shown in FIG. 8) of between 1.0 and 1.65 foot pounds per degree of compression. (While the spring constants are high, it must be remembered that the maximum spring travel may be only 0.1 inches.) The adjustment of the spring constants for a spring of a given wire diameter and overall diameter is typically performed by adjusting the number of turns in the springs. The springs thus simulate the in vitro physiologic disc stiffness in a sagittal plane (i.e. in a front to rear vertical plane through the spine).

It will be seen from FIGS. 6 and 7, that there is a clearance 104 between the hinge pin 66 and the outer elliptical apertures 60, 62. This clearance allows a small amount of side to side rocking of the upper and lower members 26, 28 with respect to each other about a vertical front to rear plane through the center of the members 26, 28 (as shown in FIG. 7). This helps to prevent damage between the parts, and as an incidental effect it allows the patient a small amount of sideways bending at the location of the artificial disc. The tapered or "cigar-shaped" ends 70 of the hinge pin 66 ensure that undue pressure is not concentrated on a single point during sideways bending, and also reduce edge stresses in the hinge pin.

An important feature of the disc 20 is that the upper and lower members 26, 28 are secured to each other and include means for rigid attachment to the vertebrae. Therefore the artificial disc 20 cannot become separated or dislodged, and the spine cannot pull apart at the location of the disc in the event of an accident.

A further feature of the embodiment shown is that the axis of hinging rotation of the upper member 26 relative to the lower member 28 is not at the center of these members, but rather is at the rear. This reduces the amount of movement which occurs near the spinal canal.

Another feature of the embodiment shown is the use of fixation points (i.e. tabs 46, 64) which are at the front and one side of the vertebrae. The front and side fixation provide good leverage relative to the forces exerted by the springs. The rear tabs 64 are preferably located (in a front to rear direction) approximately at the axis of rotation of the hinging motion.

The artificial disc 20 is made of biocompatible metal such as a suitable titanium alloy (typically titanium-6 aluminum-4 vanadium ELI alloy), or a cobalt chrome molybdenum alloy. Because of the strength of these metals, the disc will have a substantial lifetime. Other bio-compatible metals may also be used. The springs 72, 74 are preferably made of the cold worked titanium-6 aluminum-4 vanadium ELI alloy and therefore have a far longer lifetime than a compressible plastic pad. The springs are also designed so that the stresses on them are low enough that they will not normally be subject to fatigue failure, i.e. they are designed so that they are sufficiently underloaded at full compression so as not to fail due to fatigue.

It will be noted that the artificial disc 20 does not allow any rotational movement about a vertical axis. However the discs shown are primarily intended for the low lumbar region of the spine, where there is very little natural rotational movement.

Reference is next made to FIGS. 9 to 16, which show another embodiment of an artificial disc according to the invention. The embodiment shown in FIGS. 9 to 16 is in many respects the same as that of FIGS. 1 to 8, and primed reference numerals indicate parts corresponding to those of FIGS. 1 to 8.

The difference between the disc 20' of FIGS. 9 to 16 and disc 20 of FIGS. 1 to 8 is the manner in which the upper and lower members 26', 28' are hinged and held together. In disc 20' the lower member 28' includes a semi-cylindrical hinge formation 106 which extends laterally across the entire rear portion of the upper surface 50'. The lower surface 32' of the upper member 26' includes a mating semi-cylindrical hinge recess 108. The recess 108 and the semi-cylindrical formation 106 cooperate to permit a hinging action of the upper and lower members 26', 28' relative to each other about their respective rear portions.

Figure 16:
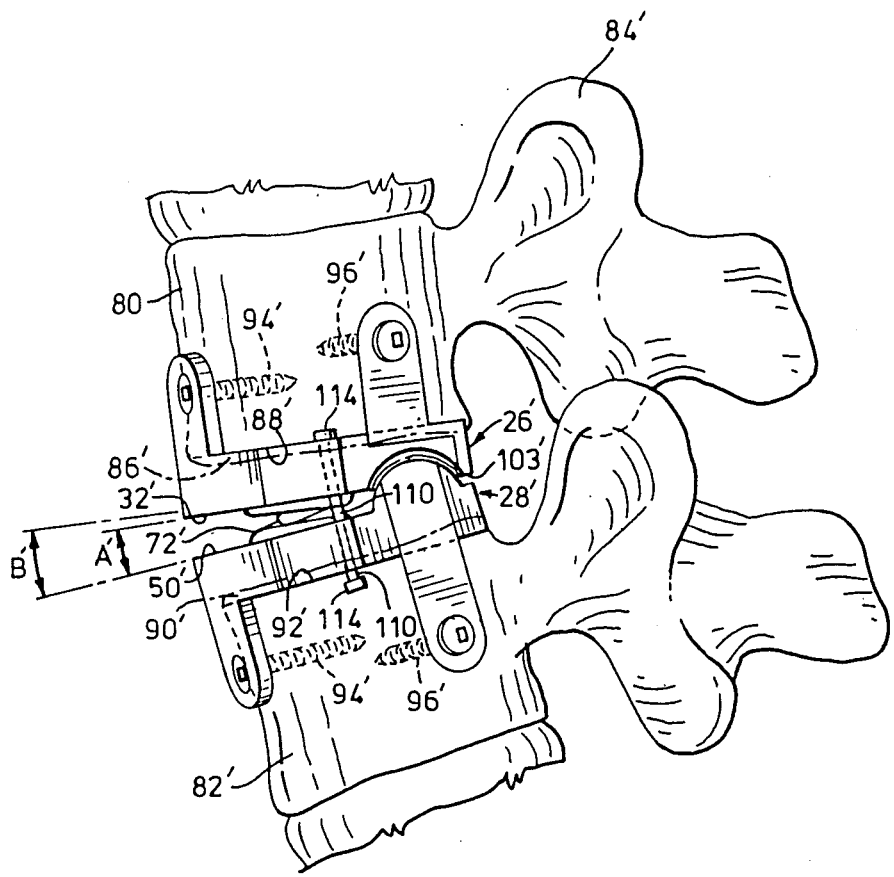
FIG. 16 is a perspective view showing the disc of FIG. 10 assembled in a human spine.

The upper and lower members 26', 28' are tied together by cables 110 which extend through holes 112 at each side of each member. The cables 110 have end caps 114 which are swaged onto each cable end to prevent the upper and lower members from pulling apart and to limit the extent of opening of the upper and lower members. As shown in FIG. 16, the cables 110 are located slightly rearwardly of the vertical axes of springs 72', 74' so that the springs and the cable together create a closing moment or torque which biases the rear ends of the upper and lower members 26', 28' together to the position shown in FIGS. 10 and 16. The normal load on the spine created by the patient's weight and muscle and ligament tension also help to bring the rear ends of members 26', 28' together.

Again and as shown in FIG. 16, reference character A' indicates the normal angle of 14 degrees when the patient is erect, and reference character B' indicates the angle of 20 degrees which occurs when the patient is leaning backwards. (The cables 110 are long enough to permit this degree of opening.) When the patient leans forward, angle A' closes to 0 degrees. Because the cables 110 are at the extreme sides of the disc 20', they are clear laterally of the vertebrae and can protrude slightly from each member 26', 28' when the angle between the members is reduced. (Such protrusion is shown for the bottom end of cable 110 in FIG. 16.)

Figure 14:
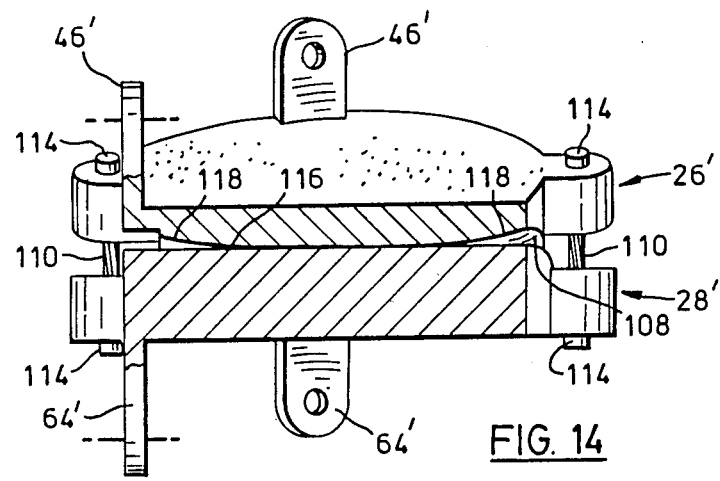
FIG. 14 is a rear view, partly in section, taken along lines 14—14 of FIG. 10.
Figure 15:
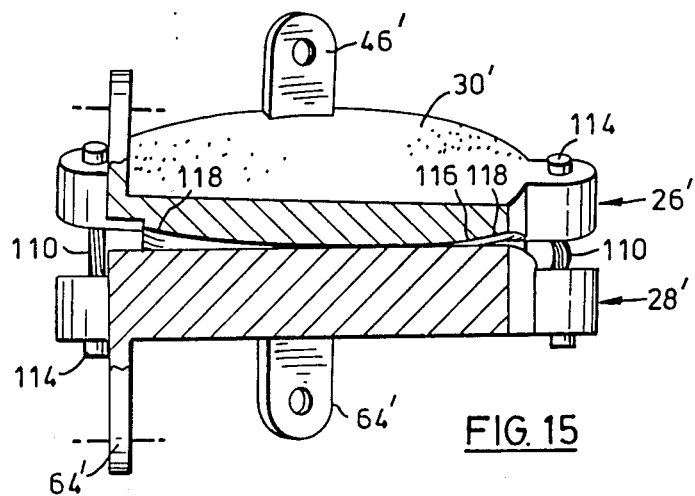
FIG. 15 is a view similar to that of FIG. 14 but showing the upper and lower members tilted sideways with respect to each other.

It will be noted as shown in FIGS. 14 and 15 that the upper surface 116 of recess 108 is convex upwardly as shown in the drawings. More particularly, the ends of the upper surface 116 curve upwardly as indicated at 118. The curved ends prevent damage when the subject leans sideways (as shown in FIG. 15) by ensuring that undue pressure is not concentrated on a single point.

Although the lower surface 32 and upper surface 50 of the upper and lower members 26, 28 respectively have been shown as substantially flat, they can of course be of any appropriate shape so long as they mate. In addition the "flat" upper and lower surfaces 30, 48 of these members can have large scale texturing, such as teeth, to help them grip the bone.

While the helical compression springs have been shown, other suitably stiff spring means can be used, e.g. torsion springs.

We claim:

1. An artificial disc for a human spine, said disc being adapted to replace a natural disc and to be located between two vertebrae, said disc comprising:
  (a) upper and lower members, each having a rear portion and a front portion,
  (b) said upper and lower members having hinge-like means adapted to permit a hinging motion of said upper and lower members relative to each other about said rear portions,
  (c) spring means positioned between said upper and lower members and biasing said front portions apart,
  (d) means securing said upper and lower members together and for permitting said hinging motion,
  (e) said upper member having means for rigidly securing said upper member to a first vertebrae above said upper member, and said lower member having means for rigidly securing said lower member to a second vertebrae below said lower member,
  (f) said means for rigidly securing said upper member comprising an upwardly extending projection adapted for mechanically locking said first member to said first vertebrae, and said means for rigidly securing said lower member comprising a downwardly extending projection adapted for mechanically locking said lower member to said second vertebrae,
  (g) said upper and lower members and said spring means all being made of a biocompatible metal alloy.

2. An artificial disc according to claim 1 wherein said upwardly extending projection comprises at least two upwardly projecting tabs adapted to overlie the side surfaces of said first vertebrae, said means for rigidly securing said upper member further comprising screws adapted to extend through said tabs and into said first vertebrae, and said downwardly extending projection comprises at least two downwardly projecting tabs adapted to overlie the side surfaces of said second vertebrae, said means for rigidly securing said lower member further comprising screws adapted to extend through said downwardly projecting tabs and into said second vertebrae.

3. An artificial disc according to claim 2 wherein for each member, one of said tabs is substantially at the center of the front of such member and a second one of said tabs is at the side of such member.

4. An artificial disc according to claim 3 wherein said second tab is substantially aligned in a front to rear direction with the axis of said hinge-like means.

5. An artificial disc according to claim 4 wherein all of said screws are of length sufficient to penetrate substantially entirely through said vertebrae.

6. An artificial disc according to claim 2 wherein said tabs have holes therein at different levels for receiving said screws, to prevent said screws from interfering with each other.

7. An artificial disc according to claim 1 wherein said hinge-like means includes means for permitting at least a limited amount of side to side rocking of said upper and lower members relative to each other about a vertical front to rear plane extending through the center of said members.

8. An artificial disc according to claim 1 wherein said means securing said upper and lower members together comprises a hinge pin.

9. An artificial disc according to claim 1 wherein said means securing said upper and lower members together comprises a hinge pin extending through aligned holes in said upper and lower members, said holes having sufficient tolerance to allow a limited amount of side to side rocking of said members relative to each other about a vertical front to rear plane extending through the center of said members.

10. An artificial disc according to claim 1 wherein said means securing said upper and lower members together comprises a hinge pin extending through aligned holes in said upper and lower members, said holes having sufficient tolerance to allow a limited amount of side to side rocking of said members relative to each other about a vertical front to rear plane extending through the center of said members, said hinge pin having tapered ends.

11. An artificial disc according to claim 1 wherein said means securing said upper and lower members together comprises a pair of cables, one at each side of said members, each cable being secured to said upper and lower members.

12. An artificial disc according to claim 11 wherein said cables extend through holes in said upper and lower members.

13. An artificial disc according to claim 1 wherein said upper and lower members have cooperating stop means at said rear portions to limit the amount of opening hinging movement between said members.

14. An artificial disc according to claim 1 wherein said spring means comprises coil springs located forwardly of said hinge-like means.

15. An artificial disc according to claim 1 wherein said spring means comprises two pairs of coil springs, said pairs being located side by side and forwardly of said hinge-like means, each pair comprising an inner coil spring and an outer coil spring concentric with said inner coil spring.

16. An artificial disc according to claim 1 wherein said upper and lower members and said spring means are all made of a bio-compatible alloy selected from titanium-6 aluminum-4 vanadium ELI alloy and a cobalt chrome molybdenum alloy.

17. An artificial disc according to claim 1 wherein said spring means has the same stiffness as the in vitro physiologic stiffness in a sagittal plane of a natural spinal disc.

18. An artificial disc according to claim 1 wherein said spring means creates a resistive torque of between 1.0 and 1.65 foot pounds per degree of compression.

* * * * *